United States Patent [19]
Kyomori et al.

[11] 3,963,781
[45] June 15, 1976

[54] METHOD OF PREPARING 2-HYDROXY-3-ALKYL-2-CYCLOPENTEN-1-ONE

[75] Inventors: Hiroyuki Kyomori, Yachiyo; Kazuhiro Sasaki, Fuchu; Mitsuhiro Takahashi, Tokyo, all of Japan

[73] Assignee: Kobayashi Perfumery Co., Ltd., Tokyo, Japan

[22] Filed: Dec. 18, 1974

[21] Appl. No.: 534,000

[30] Foreign Application Priority Data
Mar. 5, 1974 Japan............................. 49-25518
Dec. 6, 1974 Japan............................. 49-139607

[52] U.S. Cl.......................... 260/586 R; 260/566 A
[51] Int. Cl.²......................................... C07C 45/00
[58] Field of Search................. 260/586 R, 566 A

[56] References Cited
OTHER PUBLICATIONS
Geissman et al., "J. Org. Chem.", vol. 11, pp. 771–772 (1946).

Weygand, "Preparative Org. Chem.," 4th ed., p. 349, (1972).

*Primary Examiner*—Norman Morgenstern
*Attorney, Agent, or Firm*—Kemon, Palmer & Estabrook

[57] ABSTRACT

A method of preparing 2-hydroxy-3-alkyl-2-cyclopenten-1-one which comprises reacting 2-alkyl-5-carboalkoxycyclopentanone with nitrite in the presence of water and alkali; rendering the reaction system acidic; and either treating the mass for hydrolysis by heating or carrying out oxime exchange reaction in the presence of an aliphatic lower carbonyl compound added as an acceptor to the acidified reaction system.

13 Claims, 1 Drawing Figure

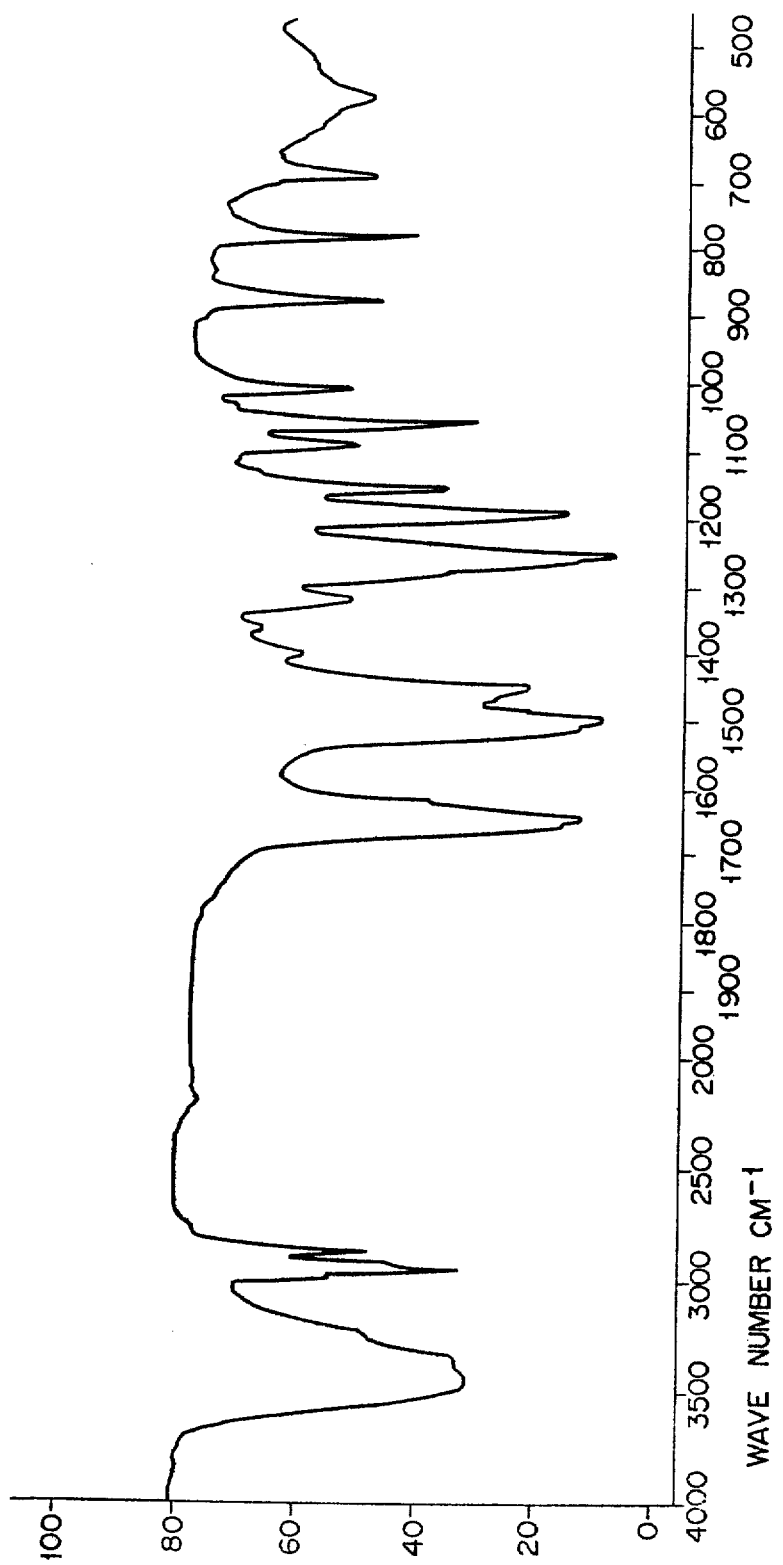

METHOD OF PREPARING 2-HYDROXY-3-ALKYL-2-CYCLOPENTEN-1-ONE

BACKGROUND OF THE INVENTION

This invention relates to a method of preparing 2-hydroxy-3-alkyl-2-cyclopenten-1-one which itself is useful as perfume, particularly as food perfume and also can be used as the raw material of other perfumes and chemicals.

As the result of the recent development of the food industry, increasing demand is made for this compound. Further, the way is being paved to prepare other perfumes and chemicals using the above-mentioned compound as a starting material.

The known processes of synthesizing said compound include (A) the process of using esters of propionic acid and esters of oxalic acid as the raw material (refer to "Nippon Nogei Kogaku Kaishi", Vol. 44, p.46, 1970) and (B) the process of using esters of adipic acid as the raw material (refer to the Japanese patent application Publication No. 14,989/66, No. 17,180/68, No. 6817/69, No. 10,493/70 and West German patent application Disclosure No. 2,005,160). However, close study has shown that the above-mentioned processes are still accompanied with drawbacks in that the processes have a low yield, and involve long and complicated reaction steps. Therefore, strong demand has been made for the development of technology capable of resolving these difficulties.

SUMMARY OF THE INVENTION

It is accordingly the object of this invention to provide an industrially advantageous method of preparing 2-hydroxy-3-alkyl-2-cyclopenten-1-one.

According to an aspect of this invention, there is provided a method of preparing 2-hydroxy-3-alkyl-2-cyclopenten-1-one having a chemical structure expressed by the general formula:

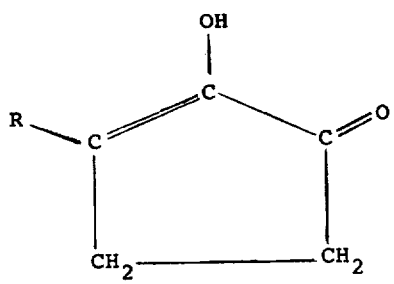

(II)

where R is a lower alkyl group, generally methyl group, ethyl group, propyl group and butyl group, which comprises reacting 2-alkyl-5-carboalkoxycyclopentanone having a chemical structure expressed by the general forumula:

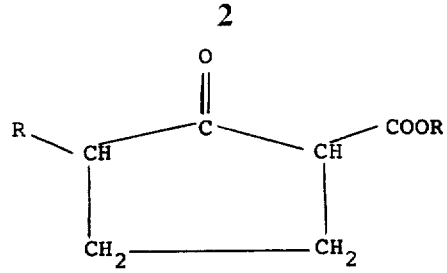

(III)

where R and R' are lower alkyl groups, generally methyl group, ethyl group, propyl group and butyl group, with nitrite in the presence of water and alkali; rendering the reaction system acidic; and thermally treating the reaction system for hydrolysis. The desired 2-hydroxy-3-alkyl-2-cyclopenten-1-one can also be prepared by, in place of thermal hydrolysis, carrying out oxime exchange reaction in the presence of an aliphatic lower carbonyl compound added as an acceptor to the acidified reaction system. According to this invention, the 2-hydroxy-3-alkyl-2-cyclopenten-1-one can be prepared by a very simple process and in high yield.

BRIEF DESCRIPTION OF THE DRAWING

The drawing is an infrared absorption spectrum of sodium salt of 2-methyl-5-carbomethoxycyclopentanone used in Examples 10 and 28 of this invention.

DETAILED DESCRIPTION OF THE INVENTION

The present inventors have found as set forth in a copending patent application Ser. No. 533,792 filed Dec. 18, 1974 an industrially advantageous method of preparing a novel compound of 2-alkyl-5-oximinocyclopentanone useful as the raw material of perfume and other chemicals whose chemical structure may be expressed by the general formula:

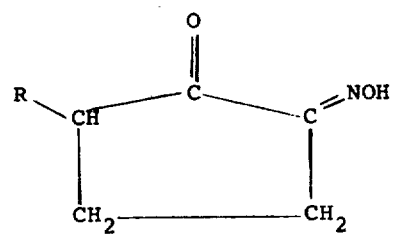

(I)

where R is a lower alkyl group, generally methyl group, ethyl group, propyl group and butyl group, by reacting 2-alkyl-5-carboalkoxycyclopentanone having a chemical structure expressed by the general formula (III) with nitrite in the presence of water and alkali, rendering the reaction liquid acidic to take place decarboxylation and prototropy. The present inventors have further found that the subject 2-hydroxy-3-alkyl-2-cyclopenten-1-one can be very easily prepared simply either by hydrolyzing the 2-alkyl-5-oximinocyclopentanone (I) or by carrying out oxime exchange reaction in the presence of an aliphatic lower carbonyl compound, and have accomplished this invention. Though, in this case, the 2-alkyl-5-oximinocyclopentanone (I) may be separated from the reaction system purposely for hydrolysis or oxime exchange reaction, yet the subject 2-hydroxy-3-alkyl-2-cyclopenten-1-one can be obtained easily and in high yield by carrying out said hydrolysis or oxime exchange reaction without drawing out said pentanone (I) from the reaction system.

2-alkyl-5-carboalkoxycyclopentanone (III) used as a starting material in the method of this invention is easily synthesized by a known process, for example, that set forth in the "Journal of Organic Chemistry", 29, 2781, 1964 by K. Sisido et al and that disclosed in said publication, 30, 183, 1965 by W. L. Meyer et al.

There will now be described the method of this invention for preparing the subject 2-hydroxy-3-alkyl-2-cyclopenten-1-one in the order of the steps.

A. Synthesis of 2-alkyl-5-oximinocyclopentanone (I).

For preparation of the 2-alkyl-5-oximinocyclopentampme (I) from 2-alkyl-5-carboalkoxycyclopentanone (III), it is necessary, as naturally expected, to activate a carbon atom occupying the fifth position of the chemical structure of the raw 2-alkyl-5-carboalkoxycyclopentanone (III) for nitrosation and hydrolyze and decarboxylate the carboalkoxy group assuming the fifth position. As the result of studies, the present inventors have found that though reaction between 2-alkyl-5-carboalkoxycyclopentanone (III) and nitrites is not smoothly effected under a neutral or acid condition, yet the aforesaid nitrosation and hydrolysis are very smoothly carried out in the presence of water and alkali and that when the reaction liquid is rendered acidic after completion of reaction, then decarboxylation and prototropy take place to precipitate the desired 2-alkyl-5-oximinocyclopentanone(I).

Nitrites used in nitrosation are not subject to any particular limitation, provided they can be applied as ordinary nitrosating agents. However, particularly preferred are potassium nitrite and sodium nitrite. Proportion of nitrites is chosen to be preferably 1 to 3 mols per mol of the raw 2-alkyl-5-carboalkoxycyclopentanone (III), or more preferably 1 to 1.1 mols. The alkalis used in this invention include sodium hydroxide, potassium hydroxide, sodium carbonate and potassium carbonate. Particularly preferred among these alkalis are sodium hydroxide and potassium hydroxide. Proportion of alkali is chosen to be preferably 1 to 3 mols, more preferably 1 to 1.5 mols and most preferably 1 to 1.2 mols per mol of the raw 2-alkyl-5-carboalkoxycyclopentanone (III).

As mentioned above, the above-mentioned reaction is carried out in the presence of water. In this case, the total amount of water used is chosen to be preferably 200 to 2000 ml per mol of the raw 2-alkyl-5-carboalkoxycyclopentanone (III), or more preferably 300 to 1200 ml. While solid nitrite and alkali and water may be separately added to the reaction system, it is convenient to add the nitrite and alkali in the form of a water solution.

Reaction temperature is generally chosen to range between 0° and 60°C, preferably between 10° and 40°C, though varying with the kind of nitrite and alkali used as well as with the number of carbon atoms contained in the R and R' groups of the raw 2-alkyl-5-carboalkoxycyclopentanone (III). Reaction time is generally chosen to be 1 to 60 hours, though varying with the number of carbon atoms contained in said R and R' groups as well as with reaction temperature.

Hydrochloric acid or sulfuric acid, for example, is adapted to be used in rendering the reaction liquid acidic for decarboxylation and prototropy after nitrosation and hydrolysis of the carboalkoxy group. When rendered acidic, the reaction system is generally chosen to be set at a lower level than room temperature, preferably a lower level than 5°C. Proportion of acid is chosen to be preferably 2 to 6 equivalents per mol of the raw 2-alkyl-5-carboalkoxycyclopentanone (III), or more preferably 2 to 2.3 equivalents.

In synthesis of 2-alkyl-5-oximinopentanone, an aqueous solution of a prescribed amount of alkali is normally added to 2-alkyl-5-carboxycyclopentanone (III) as the first step. Addition of an aqueous solution of alkali results in precipitation of white crystals. Various studies have shown said white crystals to be alkali metal (like sodium and potassium) salt of 2-alkyl-5-carboalkoxycyclopentanone (III). These white crystals indicate an infrared spectrum (drawing) which completely coincides with that of alkali metal salt of the 2-alkyl-5-carboalkoxycyclopentanone obtained by a process which omits neutralization of the catalyst alkali with acid from the process of K. Sisido et al (disclosed in the "Journal of Organic Chemistry", 27, 2781, 1964) which consists in isomerizing 2-alkyl-2-carboalkoxycyclopentanone with alkali alcoholate into 2-alkyl-5-carboalkoxycyclopentanone. Where the alkali metal salt of 2-alkyl-5-carboalkoxycyclopentanone thus obtained is substituted for 2-alkyl-5-carboalkoxycyclopentanone as a starting material in a state suspended in water and, if necessary, mixed with a small amount of alkali and with nitrite and further with acid to render the reaction liquid acidic, then the desired 2-alkyl-5-oximinocyclopentanone (I) can be produced in as good yield as in the above-mentioned case.

When the 2-alkyl-5-oximinocyclopentanone (I) is subjected to nitrosation and hydrolysis, these reactions may be effected in the presence of solvents such as methanol, ethanol, dioxane or tetrahydrofuran, insofar as said nitrosation and hydrolysis are not obstructed.

B. Synthesis of 2-hydroxy-3-alkyl-2-cyclopenten-1-one (I). The crystalline 2-alkyl-5-oximinocyclopentanone (I) precipitated in the above-mentioned step (A) is thermally hydrolyzed in a separate acid aqueous solution. The hydrolyzed mass is extracted by a proper solvent, for example, ether, chloroform, or methylene dichloride. The solvent is distilled out, easily providing high purity 2-hydroxy-3-alkyl-2-cyclopenten-1-one (II). Hydrolysis of the oximino group is generally effected at a temperature of 40°C to a reflux temperature of about 100°C, though said temperature may vary with, for example, the number of carbon atoms included in the group R of the general formula and the kind and concentration of the acid used. Particularly where the crystals of 2-alkyl-5-oximinocyclopentanone (I) are added to an acid aqueous solution, and the hydrolyzed mass is steam distilled, followed by extraction with a proper solvent, then purer 2-hydroxy-3-alkyl-2-cyclopenten-1-one is obtained in extremely high yield.

Hydrochloric acid or sulfuric acid, for example, is preferred for use in the above-mentioned hydrolysis. Addition of such acid is chosen to be preferably 0.3 to 5.0 or more preferably 0.5 to 3.0 equivalents per mol of the 2-alkyl-5-oximinocyclopentanone (I). The total requirement of water is chosen to be preferably 80 to 3000, or more preferably 200 to 1600 ml per mol of said pentanone (I).

The subject 2-hydroxy-3-alkyl-2-cyclopenten-1-one (II) can also be efficiently prepared by carrying out oxime exchange reaction in the presence of an aliphatic lower carbonyl compound added as an acceptor to the acid aqueous solution containing said pentanone (I).

Preferred among the aliphatic lower carbonyl compounds added as acceptors for the oxime exchange reaction carried out in the method of this invention are water soluble compounds like aliphatic lower aldehydes such as formaldehyde, acetaldehyde, propionaldehyde and butylaldehyde and aliphatic lower ketones such as acetone and methylethyl ketone or combinations of these compounds. Most common is formaldehyde which is used in the form of an aqueous solution or formalin. An aliphatic lower carbonyl compound used as an acceptor is added, as naturally expected, in an amount chosen to be more than 1.0 or generally 1.1 to 10 mols, or more preferably 3 to 6 mols per mol of the 2-alkyl-5-oximinocyclopentanone (I). These molar values are the same on the basis of 2-alkyl-5-carboalkoxycyclopentanone (III).

According to the method of this invention, oxime exchange reaction is carried out in an acid aqueous solution. Hydrochloric acid or sulfuric acid, for example, is adapted to be used in rendering the reaction system acidic. Such acid is added in an amount chosen to be preferably 0.3 to 5.0 or more preferably 0.5 to 3.0 equivalents per mol of the 2-alkyl-5-oximinocyclopentanone (I). The total amount of water added to the reaction system is chosen to be preferably 80 to 3000, or more preferably 200 to 1600 ml per mol of the 2-alkyl-5-oximinocyclopentanone (I).

Oxime exchange reaction is generally carried out at a temperature of 0° to 50°C, or more preferably 10° to 40°C and for a period ranging between 2 hours and 3 days, though said temperature and period of oxime exchange reaction may vary with the number of carbon atoms included in the group R of the formulas (I) and (II), the kind and concentration of acid added to the reaction system and the kind and concentration of an aliphatic lower carbonyl compound used as an acceptor. This oxime exchange reaction provides the subject 2-hydroxy-3-alkyl-2-cyclopenten-1-one (II) more efficiently. Among the homologues of 2-hydroxy-3-alkyl-2-cyclopenten-1-one, the type, where the R of the general formula (II) is a methyl group, namely 2-hydroxy-3-methyl-2-cyclopenten-1-one is most valuable as perfume and most widely accepted in practice. What is surprising is that where formaldehyde, for example, is used as an acceptor, then more than half the subject product is precipitated as crystals from the reaction solution with such high quality as eliminates the necessity of carrying out any purification. Therefore, the subject product can be easily provided simply by filtering the precipitates from the reaction solution. The remainder of the subject product can be completely extracted by treating a filtrate left after removal of the above crystals with a proper solvent, for example, chloroform. Where, therefore, the solvent is distilled out of the extract and the resultant crude product is purified by a simple process, for example, recrystallization, then it is possible to obtain the desired product with as high quality as the first crystals.

The above-mentioned hydrolysis or oxime exchange reaction can be carried out without removing 2-alkyl-5-oximinocyclopentanone (I) from the reaction system. Namely, 2-alkyl-5-carboalkoxycyclopentanone (III) has only to be reacted with nitrite in the presence of water and alkali, or it is possible to react alkali salt of said pentanone (III) with nitrite in the presence of water and if necessary, with addition of a small amount of alkali. After that, where 2-alkyl-5-oximinocyclopentanone (I) precipitated after rendering the reaction liquid acidic by addition of, for example, hydrochloric acid or sulfuric acid is heated for hydrolysis or is mixed with an aliphatic lower carbonyl compound as an acceptor for oxime exchange reaction without being removed from the reaction system, then the desired 2-hydroxy-3-alkyl-2-cyclopenten-1-one is obtained. This process is very advantageous, because it involves simple steps.

In this case, proportion of acid contained in the reaction system is chosen to be preferably 2.3 to 11 equivalents, or more preferably 2.5 to 5.3 equivalents per mol of the raw 2-alkyl-5-carboalkoxycyclopentanone (III).

This invention will be more fully understood by reference to the examples which follow.

EXAMPLE 1

A solution prepared by dissolving 2.2g of sodium hydroxide in 20 ml of water was dripped at a lower temperature than 20°C into 7.8g of 2 methyl-5-carbomethoxycyclopentanone. A solution prepared by dissolving 3.44g of sodium nitrite in 10 ml of water was further add to the reaction system. The mass was stirred 3 hours at 40°C and then cooled to a lower temperature than 5°C. Upon addition of 18.3 ml of 6N hydrochloric acid, crystals were immediately precipitated. Upon washing the crystals with a small amount of cold water after filtration, 4.8g (76% yield) of white crystals of 2-methyl-5-oximinocyclopentanone were obtained. The white crystals displayed the following physicochemical properties:

Melting point: 51 to 53°C (corrected)
Nuclear magnetic resonance (NMR): 1.18 (3H, d)
(CDCL$_3$ solution, ppm) 1.3 to 1.9 (1H, m)
2.1 to 3.3 (4H, m)
8.65 (1H, s)
Infrared absorption (IR): 3575, 3395, 3155 (OH),
(KBr tablet, cm$^{-1}$) 1735 (C=O), 1643 (C=N)
Analysis of elements: C 56.30%
H 7.05%
C 56.88% } as calculated from
H 7.14% } C$_6$H$_9$NO$_2$ 6.35g of the crystalline 2-methyl-5-oximinocyclopentanone thus obtained was mixed with 20ml of water, followed by addition of 22 ml of 6N sulfuric acid. The whole mass was refluxed one hour. After the mass was cooled, said mass was twice subjected to extraction with 150 ml of chloroform. The chloroform extract was washed twice with 30 ml of cold water and also twice with 30 ml of a saturated aqueous solution of sodium bicarbonate and further once with 30 ml of cold water, followed by drying with anhydrous sodium sulfate. Thereafter the chloroform was distilled out under vacuum, providing 3.5g crude crystals of the desired 2-hydroxy-3-methyl-2-cyclopenten-1-one. The crude product was recrystallized from water, obtaining 3.1g of white crystals in 42% yield based on the raw 2-methyl-5-carboalkoxycyclopentanone. The white crystals displayed the following physicochemical properties:

Melting point: 107 to 108°C (corrected)
NMR: 2.00 (3H, s)

| (CDCl₃, ppm) | -continued |
|---|---|
| | 2.42 (3H, s) |
| | 2.86 (1H, s) |
| IR : | 3325 (OH) |
| (KBr tablet, cm⁻¹) | |
| | 1700 (C=O) |
| | 1648 (C=C) |
| Analysis of elements : | C 64.30% |
| | H 7.15% |
| | C 64.27%  as calculated from |
| | H 7.19%  C₈H₈O₂ |

EXAMPLE 2

6.35g of the crystalline 2-methyl-5-oximinocyclopentanone obtained from 2-methyl-5-carbomethoxycyclopentanone in the same manner as in Example 1 was mixed with 20 ml of water, followed by addition of 22 ml of 6N sulfuric acid. The whole mass was subjected to steam distillation. 500 ml of the distillate was subjected three times to extraction with 200 ml of chloroform. The chloroform extract was dried with anhydrous sodium sulfate. Crystals obtained after distillation of the chloroform under vacuum were recrystallized from water, providing 5.2g of white crystals of the desired 2-hydroxy-3-methyl-2-cyclopenten-1-one in 71% yield based on the raw 2-methyl-5-carbomethoxycyclopentanone. The white crystals indicated the same physicochemical properties as in Example 1.

EXAMPLE 3

A solution prepared by dissolving 1.47g of sodium hydroxide in 28 ml of water was dripped at a lower temperature than 20°C into 5.7g of 2-ethyl-5-carbomethoxycyclopentanone. A solution prepared by dissolving 2.3g of sodium nitrite in 7 ml of water was further added to the reaction system. The mass was stirred 24 hours at 40°C, and then cooled to a lower temperature than 5°C. Upon addition of 14.7 ml of 6N hydrochloric acid, crystals were immediately precipitated. Upon washing the crystals with a small amount of cold water after filtration, 3.4g (72% yield) of white crystals of 2-ethyl-5-oximinocyclopentanone were obtained. The white crystals indicated the following physicochemical properties.

| Melting point : | 41 to 40°C (corrected) |
|---|---|
| NMR : | 0.95 (3H, t) |
| (CDCl₃ solution, ppm) | |
| | 1.2 to 1.9 (3H, m) |
| | 1.9 to 3.2 (4H, m) |
| | 9.4 (1H, s) |
| IR : | 3520, 3150 (OH), 1730 (C=O), |
| (KBr tablet, cm⁻¹) | 1640 (C=N) |
| Analysis of elements : | C 59.21% |
| | H 7.61% |
| | C 59.56%  as calculated from |
| | H 7.85%  C₇H₁₁NO₂ |

7.05g of the crystalline 2-ethyl-5-oximinocyclopentanone thus obtained was subjected to steam distillation in the same manner as in 2-methyl-5-oximinocyclopentanone of Example 2. 500 ml of the distillate was subjected three times to extraction with 200 ml of chloroform. The chloroform extract was dried with anhydrous sodium sulfate and the chloroform was distilled out under vacuum, quantitatively providing faintly brown oily crude product. Said crude product was further subjected to distillation under vacuum, producing 5.4g of colorless liquid 2-hydroxy-3-ethyl-2-cyclopenten-1-one in 62% yield based on the raw 2-ethyl-5-carbomethoxycyclopentanone. When the colorless liquid was cooled, said liquid was solidified. The final product showed the following physicochemical properties:

| Boiling point : | 86° to 87°C/0.5 mm Hg |
|---|---|
| Melting point : | 41° to 42°C (corrected) |
| NMR : | 1.13 (3H, t) |
| (CDCl₃, ppm) | |
| | 2.40, 2.42 (6H, s, q) |
| | 6.50 (1H, s) |
| IR : | 3330 (OH) |
| (KBr tablet, cm⁻¹) | |
| | 1690 (C=O) |
| | 1650 (C=C) |
| Analysis of elements : | C 66.38% |
| | H 7.82% |
| | C 66.64%  as calculated from |
| | H 7.99%  C₇H₁₀O₂ |

EXAMPLE 4

A solution prepared by dissolving 1.47g of sodium hydroxide in 28 ml of water was dripped at a lower temperature than 20°C into 6.13g of 2-n-propyl-5-carbomethoxycyclopentanone. A solution prepared by dissolving 2.3g of sodium nitrite in 7 ml of water was further added to the reaction system. The mass was stirred 6 hours at 40°C and then cooled to a lower temperature than 5°C. Upon addition of 14.7 ml of 6N hydrochloric acid, crystals were immediately precipitated. Upon washing the crystals with a small amount of cold water after filtration, 3.6g (70% yield) of white crystals of 2-n-propyl-5-oximinocyclopentanone were obtained. The white crystals showed the following physicochemical properties:

| Melting point : | 55 to 57°C (corrected) |
|---|---|
| NMR : | 0.92 (3H, t) |
| (CDCl₃ solution, ppm) | |
| | 1.1 to 2.0 (5H, m) |
| | 2.0 to 3.2 (4H, m) |
| | 8.9 (1H, s) |
| IR : | 3570, 3395, 3155 (OH), 1735 (C=O), |
| (KBr tablet, cm⁻¹) | 1642 (C=N) |
| Analysis of elements : | C 61.75% |
| | H 8.50% |
| | C 61.92%  as calculated from |
| | H 8.44%  C₈H₁₃NO₂ |

7.75g of the 2-n-propyl-5-oximinocyclopentanone thus obtained was subjected to treatment in the same manner as in Example 2, providing 6.0g of colorless liquid 2-hydroxy-3-n-propyl-2-cyclopenten-1-one in 60% yield based on the raw 2-n-propyl-5-carbomethoxycyclopentanone. When the colorless liquid was cooled said liquid was solidified. The subject product displayed the following physicochemical properties:

| Boiling point : | 84° to 85°C/0.5 mm Hg |
|---|---|
| Melting point : | 55° to 57°C (corrected) |
| NMR : | 0.94 (3H, t) |
| (CDCl₃, ppm) | |
| | 1.2 to 1.9 ( 2H, m) |
| | 2.38, 2.40 (6H, q, s) |
| | 6.43 (1H, s) |
| IR : | 3260 (OH) |
| (KBr tablet, cm⁻¹) | |
| | 1695 (C=O) |
| | 1650 (C=C) |
| Analysis of elements : | C 68.50% |
| | H 8.55% |
| | C 68.54%  as calculated from |
| | H 8.63%  C₈H₁₂O₂ |

EXAMPLE 5

A solution prepared by dissolving 1.47g of sodium hydroxide in 28 ml of water was dripped at a lower temperature than 20°C into 5.7g of 2-methyl-5-carbethoxycyclopentanone. A solution prepared by dissolving 2.3g of sodium nitrite in 7 ml of water was further added to the reaction system. The mass was stirred 3 hours at 40°C and then cooled to a lower temperature than 5°C. Upon addition of 14.7 ml of 6N hydrochloric acid, crystals were immediately precipitated. Upon washing the crystals with a small amount of cold water after filtration, 3.2g (75% yield) of white crystals of 2-methyl-5-oximinocyclopentanone were obtained. The white crystals indicated the same physicochemical properties as in Example 1.

Where the 2-methyl-5-oximinocyclopentanone thus prepared was hydrolyzed in the same manner as in Example 2, white crystals of 2-hydroxy-3-methyl-2-cyclopenten-1-one was obtained in 70% yield based on the raw 2-methyl-5-carbethoxycyclopentanone. Said white crystals indicated the same properties as in Example 1.

EXAMPLE 6

A solution prepared by dissolving 1.47g of sodium hydroxide in 28 ml of water was dripped at a lower temperature than 20°C into 5.2g of 2-methyl-5-carbomethoxycyclopentanone. A solution prepared by dissolving 3.0g of potassium nitrite in 7 ml of water was further added to the reaction system. The following operation was carried out in the same manner as in Example 5, providing 3.2g (75% yield) of white crystals of 2-methyl-5-oximinocyclopentanone. The white crystals indicated the same physicochemical properties as in Example 1.

Where the 2-methyl-5-oximinocyclopentanone thus prepared was hydrolyzed in the same manner as in Example 2, white crystals of 2-hyroxy-3-methyl-2-cyclopenten-1-one was obtained in 70% yield based on the raw 2-methyl-5-carbomethoxycyclopentanone. Said white crystals indicated the same properties as in Example 2.

EXAMPLE 7

A solution prepared by dissolving 2.1g of potassium hydroxide in 28 ml of water was dripped at a lower temperature than 20°C into 5.2g of 2-methyl-5-carbomethoxycyclopentanone. The following operation was effected in the same manner as in Example 5, providing 3.1g (73% yield) of white crystals of 2-methyl-5-oximinocyclopentanone. The white crystals presented the same physicochemical properties as in Example 1.

Where the 2-methyl-5-oximinocyclopentanone thus prepared was hydrolyzed in the same manner as in Example 2, white crystals of 2-hydroxy-3-methyl-2-cyclopenten-1-one was obtained in 68% yield based on the raw 2-methyl-5-carbomethoxycyclopentanone. Said white crystals indicated the same properties as in Example 1.

EXAMPLE 8

A solution prepared by dissolving 1.47g of sodium hydroxide in 28 ml of water was dripped at a lower temperature than 20°C into 5.2g of 2-methyl-5-carbomethoxycyclopentanone. A solution prepared by dissolving 2.3g of sodium nitrite in 7 ml of water was further added to the reaction system. The mass was stirred 3 hours at 40°C, and then cooled to a lower temperature than 5°C, followed by addition of 14.7 ml of 6N sulfuric acid. The following operation was performed in the same manner as in Example 5, obtaining 3.1g (73% yield) of white crystals of 2-methyl-5-oximinocyclopentanone. The white crystals displayed the same physicochemical properties as in Example 1.

Where the 2-methyl-5-oximinocyclopentanone thus prepared was hydrolyzed in the same manner as in Example 2, white crystals of 2-hydroxy-3-methyl-2-cyclopenten-1-one was obtained in 68% yield based on the raw 2-methyl-5-carbomethoxycyclopentanone. Said white crystals indicated the same properties as in Example 1.

EXAMPLE 9

A solution prepared by dissolving 1.47g of sodium hydroxide in 28 ml of water was dripped at a lower temperature than 20°C into 6.13g of 2-methyl-5-carbo-n-propoxycyclopentanone. A solution prepared by dissolving 2.3g of sodium nitrite in 7 ml of water was further added to the reaction system. The mass was stirred 4 hours at 40°C and cooled to a lower temperature than 5°C, followed by addition of 14.7 ml of 6N hydrochloric acid. The following operation was conducted in the same manner as in Example 5, providing 2.9g (68% yield) of white crystals of 2-methyl-5-oximinocyclopentanone. The white crystals indicated the same physicochemical properties as in Example 1.

Where the 2-methyl-5-oximinocyclopentanone thus prepared was hydrolyzed in the same manner as in Example 2, white crystals of 2-hydroxy-3-methyl-2-cyclopenten-1-one was obtained in 63% yield based on the raw 2-methyl-5-carbo-n-propoxycyclopentanone. Said white crystals indicated the same properties as in Example 1.

EXAMPLE 10

A solution prepared by dissolving 1.47g of sodium hydroxide in 28 ml of water was dripped at a lower temperature than 20°C into 5.2g of 2-methyl-5-carbomethoxycyclopentanone. The white crystals which were immediately precipitated were filtered and washed with a small amount of ether, followed by drying. Then white crystals of sodium salt of 2-methyl-5-carbomethoxycyclopentanone were quantitatively obtained. The latter white crystals displayed an infrared spectrum (KBr tablet) as shown in the drawing.

When 2.49g of white crystals of sodium salt of 2-methyl-5-carbomethoxycyclopentanone were suspended in cold water and rendered acidic by adding dilute hydrochloric acid, then the mass was separated into an oil layer and a water layer. The water layer thus separated was twice subjected to extraction with 30 ml of ether. A mixture of the oil layer and ether-extract was washed first with 5 ml of saturated aqueous solution of sodium bicarbonate and then twice with 10 ml of water. The mass was dried with anhydrous sodium sulfate and the solvent was recovered under vacuum, quantitatively producing colorless oily crude 2-methyl-5-carbomethoxycyclopentanone. This product presented exactly the same infrared spectrum (liquid film) as that of the initial raw 2-methyl-5-carbomethoxycyclopentanone.

When 2-methyl-2-carbomethoxycyclopentanone was isomerized into 2-methyl-5-carbomethoxycyclopentanone in accordance with the process proposed by K. Sisido et al in the "Journal of Organic Chemistry", 29, 2781, 1964 (cf. the article by W. L. Meyer et al given in the "Journal of Organic Chemistry", 30, 183, 1965) and the resultant reaction liquid was cooled without neutralizing the catalyst of sodium in the last step, then sodium salt of 2-methyl-5-carbomethoxycyclopentanone was produced in higher yield than 80%. Said sodium salt showed the exactly the same infrared spectrum (KBr tablet) as that of the previously mentioned crystals of sodium salt of 2-methyl-5-carbomethoxycyclopentanone obtained by treating 2-methyl-5-carbomethoxycyclopentanone with an aqueous solution of sodium hydroxide.

A solution prepared by dissolving 0.2g of sodium hydroxide in 40 ml of water was dripped at a lower temperature than 20°C into 8.9g of sodium salt of 2-methyl-5-carbomethoxycyclopentanone obtained in the above-mentioned manner.

A solution prepared by dissolving 3.45g of sodium nitrite in 10 ml of water was further added to the reaction system. The mass was stirred 6 hours at room temperature and then cooled to a lower temperature than 5°C, followed by addition of 18.3 ml of 6N hydrochloric acid. The following operations were carried out in the same manner as in Example 1, providing 4.7g (74% yield) of white crystals of the desired 2-methyl-5-oximinocyclopentanone. The white crystals displayed the same physicochemical properties as in Example 1.

Where the 2-methyl-5-oximinocyclopentanone thus prepared was hydrolyzed in the same manner as in Example 2, white crystals of 2-hydroxy-3-methyl-2-cyclopenten-1-one was obtained in 69% yield based on the sodium salt of 2-methyl-5-carbomethoxycyclopentanone. Said white crystals indicated the same properties as in Example 1.

EXAMPLE 11

3.18g of 2-methyl-5-oximinocyclopentanone prepared from 2-methyl-5-carbomethoxycyclopentanone in the same manner as in Example 1 was first mixed with 12.5 ml of water, then with 6.2 ml of concentrated hydrochloric acid at a lower temperature than 20°C and finally with 12 ml of formalin. The whole mass was stirred 5 hours at room temperature. 1.7g of while crystals precipitated upon cooling of the reaction liquid to a lower temperature than 5°C as filtered and collected. The filtrate was twice subjected to extraction with 50 ml of chloroform each time. Two chloroform extracts were combined and washed twice first with 5 ml of a saturated aqueous solution of sodium bicarbonate and then with 5 ml of water, followed by drying with anhydrous sodium sulfate. The chloroform was distilled out under vacuum, providing 0.9g of while crystals. A mixture of the former lot of white crystals weighing 1.7g and the latter lot of white crystals weighing 0.9g was recrystallized from water, providing 2.4g of white crystals of the desired high quality 2-hydroxy-3-methyl-2-cyclopenten-1-one in 65% yield based on the raw 2-methyl-5-carbomethoxycyclopentanone. The finally produced white crystals indicated the same physicochemical properties as in Example 1.

EXAMPLE 12

4.7g of 2-ethyl-5-oximinocyclopentanone obtained from 2-ethyl-5-carbomethoxycyclopentanone in the same manner as in Example 3 was mixed first with 21 ml of water, then with 12.2 ml of 6N hydrochloric acid at a lower temperature than 20°C and finally with 9 ml of formalin. The whole mass was stirred 5 hours at room temperature. The reaction liquid was twice subjected to extraction with 100 ml of chloroform each time. Two chloroform extracts were combined and washed twice first with 10 ml of a saturated aqueous solution of sodium bicarbonate and then with 10 ml of water, followed by drying with anhydrous sodium sulfate. The chloroform was distilled out under vacuum, quantitatively providing a faintly brown oily crude product. The crude product was further subjected to vacuum distillation, obtaining 3.6g of the desired colorless liquid 2-hydroxy-3-ethyl-2-cyclopenten-1-one in 62% yield based on the raw 2-ethyl-5-carbomethoxycyclopentanone. When the colorless liquid was cooled, said liquid was solidified. The subject 2-hydroxy-3-ethyl-2-cyclopenten-1-one presented the same physicochemical properties as in Example 3.

EXAMPLE 13

5.17g of 2-n-propyl-5-oximonocyclopentanone obtained from 2-n-propyl-5-carbomethoxycyclopentanone in the same manner as in Example 4 was mixed first with 30 ml of water, then 14.7 ml of 6N hydrochloric acid at a lower temperature than 20°C and finally with 9 ml of formalin. The whole mass was stirred 6 hours at room temperature. The reaction liquid was treated in the same manner as in Example 12, providing 4.2 g of the desired colorless liquid 2-hydroxy-3-n-propyl-2-cyclopenten-1-one in 63% yield based on the raw 2-n-propyl-5-carbomethoxycyclopentanone. When the colorless liquid was cooled, said liquid was solidified. The subject 2-hydroxy-3-n-propyl-2-cyclopenten-1-one presented the same physicochemical properties as in Example 4.

EXAMPLE 14

3.81g of 2-methyl-5-oximinocyclopentanone obtained from 2-methyl-5-carbomethoxycyclopentanone in the same manner as in Example 1 was mixed first with 5 ml of water, then with 6 ml of 6N hydrochloric acid at a lower temperature than 20°C and finally with 5.0g of acetaldehyde of 80% purity. The whole mass was stirred 24 hours at room temperature. 1.5g of white crystals precipitated upon cooling the reaction liquid to a lower temperature than 5°C were filtered and collected. The filtrate was twice subjected to extraction with 50 ml of chloroform each time. Two chloroform extracts were combined and treated in the same manner as in Example 11, providing 1.3g of white crystals. The first lot of white crystals weighing 1.5g and the second lot of white crystals weighing 1.3g were put together. The whole mass was recrystallized from water, providing 2.7g of white crystals of the desired 2-hydroxy-3-methyl-2-cyclopenten-1-one in 61% yield based on the raw 2-methyl-5-carbomethoxycyclopentanone. The finally produced white crystals displayed the same physicochemical properties as in Example 1.

EXAMPLE 15

3.18g of 2-methyl-5-oximinocyclopentanone obtained from 2-methyl-5-carbomethoxycyclopentanone in the same manner as in Example 1 was mixed first with 25 ml of water, then with 6.2 ml of concentrated hydrochloric acid at a lower temperature than 20°C and finally with 9.3g of acetone. The whole mass was stirred 15 hours at a temperature of 35° to 40°C. The reaction liquid was cooled to a lower temperature than 5°C, followed by stirring of one hour. 0.7g of precipitated white crystals was filtered and collected. The filtrate was twice subjected to extraction with 50 ml of chloroform each time. The whole mass of two chloroform extracts were treated in the same manner as in Example 11, providing 1.0g of white crystals. The former lot of white crystals weighing 0.7g and the latter lot of white crystals weighing 1.0g were put together. The whole mass was recrystallized from water, providing 1.5g of white crystals of the desired 2-hydroxy-3-methyl-2-cyclopenten-1-one in 41% yield based on the raw 2-methyl-5-carbomethoxycyclopentanone. The finally produced white crystals showed the same physicochemical properties as in Example 1.

EXAMPLE 16

3.18g of 2-methyl-5-oximinocyclopentanone obtained from 2-methyl-5-carbomethoxycyclopentanone in the same manner as in Example 1 was mixed first with 25 ml of water, then with 6.2 ml of concentrated hydrochloric acid at a lower temperature than 20°C and finally with 11.6g of methylethylketone. The whole mass was stirred 15 hours at a temperature of 35° to 40°C. The reaction liquid was twice subjected to extraction with 50 ml of chloroform. The whole mass of two chloroform extracts was washed twice first with 10 ml of a saturated aqueous solution of sodium bicarbonate and then with 10 ml of water, followed by drying with anhydrous sodium sulfate. The chloroform was distilled out under vacuum, providing 1.8g of white crystals. Said white crystals were recrystallized from water, obtaining 1.5g of white crystals of the desired 2-hydroxy-3-methyl-2-cyclopenten-1-one in 41% yield based on the raw 2-methyl-5-carbomethoxycyclopentanone. The recrystallized product indicated the same physicochemical properties as in Example 1.

EXAMPLE 17

A solution prepared by dissolving 2.2g of sodium hydroxide in 20 ml of water was dripped into 7.8g of 2-methyl-5-carbomethoxycyclopentanone at a lower temperature than 20°C. The mass was mixed with a solution prepared by dissolving 3.44g of sodium nitrite in 10 ml of water. The mixture was stirred 3 hours at 40°C, followed by cooling to a lower temperature than 5°C. After 22 ml of 6N sulfuric acid was added, the whole mass was subjected to steam distillation. 500 ml of distillate was subjected three times to extraction with 200 ml of chloroform each time, followed by drying chloroform extracts with anhydrous sodium sulfate. The chloroform was distilled out under vacuum, quantitatively providing white crystals. These crystals were further recrystallized from water, obtaining 5.1g of white needle-like crystals of the desired 2-hydroxy-3-methyl-2-cyclopenten-1-one in 91% yield based on the 2-methyl-5-carbomethoxycyclopentanone. The white needle-like crystals showed the same physicochemical properties as in Example 1.

EXAMPLE 18

A solution prepared by dissolving 1.47g of sodium hydroxide in 28 ml of water was dripped into 5.7g of 2-ethyl-5-carbomethoxycyclopentanone at a lower temperature than 20°C. A solution prepared by dissolving 2.3g of sodium nitrite in 7 ml of water was further added to the mixture. The whole mass was stirred 24 hours at 40°C and cooled to a lower temperature than 5°C, followed by addition of 14.7 ml of 6N sulfuric acid. 500 ml of a distillate derived from steam distillation of the entire mass was subjected three times to extraction with 200 ml of chloroform each time. The extract was treated in the same manner as in Example 17, providing 3.5g of the desired colorless liquid 2-hydroxy-3-ethyl-2-cyclopenten-1-one in 83% yield based on the raw 2-ethyl-5-carbomethoxycyclopentanone. The final product displayed the same physicochemical properties as in Example 3.

EXAMPLE 19

A solution prepared by dissolving 1.47g of sodium hydroxide in 28 ml of water was dripped at a lower temperature than 20°C into 6.13g of 2-n-propyl-5-carbomethoxycyclopentanone. A solution prepared by dissolving 2.3g of sodium nitrite in 7 ml of water was further added to the mixture. The whole mass was stirred 6 hours at 40°C, followed by cooling to a lower temperature than 5°C. After addition of 14.7 ml of 6N sulfuric acid, the entire mass was subjected to steam distillation. The following operation was conducted in the same manner as in Example 17, providing 3.9g of the desired colorless liquid 2-hydroxy-3-n-propyl-2-cyclopenten-1-one in 84% yield based on the raw 2-n-propyl-5-carbomethoxycyclopentanone. The final product showed the same physicochemical properties as in Example 4.

EXAMPLE 20

A solution prepared by dissolving 1.47g of sodium hydroxide in 28 ml of water was dripped at a lower temperature than 20°C into 5.7g of 2-methyl-5-carbethoxycyclopentanone. A solution prepared by dissolving 2.3g of sodium nitrite in 7 ml of water was added to the mixture. The whole mass was stirred 3 hours at 40°C, followed by cooling to a lower temperature than 5°C. After addition of 14.7 ml of 6N sulfuric acid, the entire mass was subjected to steam distillation. The following operation was carried out in the same manner as in Example 17, producing 5.0g of white needle-like crystals of the desired 2-hydroxy-3-methyl-2-cyclopenten-1-one in 89% yield based on the raw 2-methyl-5-carbethoxycyclopentanone. The final product presented the same physicochemical properties as in Example 1.

EXAMPLE 21

A solution prepared by dissolving 2.2g of sodium hydroxide in 40 ml of water was dripped at a lower temperature than 20°C into 7.8g of 2-methyl-5-carbomethoxycyclopentanone. A solution prepared by dissolving 3.45g of sodium nitrite in 10 ml of water was further added to the mixture. The whole mass was stirred 6 hours at room temperature, followed by cooling to a lower temperature than 5°C. After addition of 13 ml of concentrated hydrochloric acid, stirring was continued 1 more hour at the same temperature, 24 ml of formalin was added to the mass, and the whole mass was further stirred 17 hours at room temperature. 2.9g of white crystals precipitated upon cooling to a lower temperature than 5°C were filtered and collected. The filtrate was twice subjected to extraction with 100 ml of chloroform each time. The mass of two chloroform extracts was washed first with 10 ml of a saturated aqueous solution of sodium bicarbonate and then twice with 10 ml of water, followed by drying with anhydrous sodium sulfate. The chloroform was distilled out under vacuum, providing 1.9g of white crystals. The former lot of white crystals weighing 2.9g and the latter lot white crystals weighing 1.9g were put together. The whole mass of said white crystals was recrystallized from water, obtaining 4.6g of white needle-like crystals of the desired 2-hydroxy-3-methyl-2-cyclopenten-1-one in 82% yield based on the raw 2-methyl-5-carbomethoxycyclopentanone. The white needle-like crystals showed the same physicochemical properties as in Example 1.

EXAMPLE 22

8.5g of 2-methyl-5-carbethoxycyclopentanone was subjected to the same reaction and treatment as in Example 21, providing 4.7g of white crystals of the desired 2-hydroxy-3-methyl-2-cyclopenten-1-one in 84% yield based on the raw 2-methyl-5-carbethoxycyclopentanone. The final crystalline product indicated the same physicochemical properties as in Example 1.

EXAMPLE 23

A solution prepared by dissolving 1.5g of sodium hydroxide in 14 ml of water was dripped at a lower temperature than 20°C into 5.7g of 2-ethyl-5-carbomethoxycyclopentanone. A solution prepared by dissolving 2.3g of sodium nitrite in 7 ml of water was further added to the mixture. The whole mass was stirred 24 hours at 40°C, followed by cooling to a lower temperature than 5°C. After addition of 12 ml of concentrated hydrochloric acid, stirring was continued 1 more hour. 9 ml of formalin were added to the mass, followed by stirring of 5 hours at room temperature. The reaction liquid was twice subjected to extraction with 100 ml of chloroform each time. The following operation was carried out in the same manner as in Example 12, obtaining 3.8g of colorless liquid 2-hydroxy-3-ethyl-2-cyclopenten-1-one in 90% yield based on the raw 2-ethyl-5-carbomethoxycyclopentanone. The final product displayed the same physicochemical properties as in Example 3.

EXAMPLE 24

A solution prepared by dissolving 1.5g of sodium hydroxide in 20 ml of water was dripped at a lower temperature than 20°C into 6.1g of 2-n-propyl-5-carbomethoxycyclopentanone. A solution prepared by dissolving 2.3g of sodium nitrite in 7 ml of water was further added to the mixture. The whole mass was stirred 6 hours at 40°C, followed by cooling to a lower temperature than 5°C. After addition of 12 ml of concentrated hydrochloric acid, stirring was continued 1 more hour. 9 ml of formalin were added to the mass, followed by stirring of 6 hours at room temperature. The reaction liquid was treated in the same operation as in Example 13, obtaining 4.3g of the desired colorless liquid 2-hydroxy-3-n-propyl-2-cyclopenten-1-one in 91% yield based on the raw 2-n-propyl-5-carbomethoxycyclopentanone. The final product showed the same physicochemical properties as in Example 4.

EXAMPLE 25

A solution prepared by dissolving 2.2g of sodium hydroxide in 40 ml of water was dripped at a lower temperature than 20°C into 9.2g of 2-methyl-5-carbo-n-propoxycyclopentanone. A solution prepared by dissolving 3.45g of sodium nitrite in 10 ml of water was further added to the mixture. The whole mass was stirred 12 hours at room temperature, and later subjected to the same reaction and treatment as in Example 21, providing 4.5g of white crystals of the desired 2-hydroxy-3-methyl-2-cyclopenten-1-one in 80% yield based on the raw 2-methyl-5-carbo-n-propoxycyclopentanone. The white crystals showed the same physicochemical properties as in Example 1.

EXAMPLE 26

A solution prepared by dissolving 2.2g of sodium hydroxide in 40 ml of water was dripped at a lower temperature than 20°C into 7.8g of 2-methyl-5-carbomethoxycyclopentanone. A solution prepared by dissolving 3.45g of sodium nitrite in 10 ml of water was further added to the mixture. The whole mass was stirred for 6 hours at room temperature, followed by cooling to a lower temperature than 5°C. After addition of 15 ml of concentrated hydrochloric acid, stirring was continued one more hour. 4.7g of propionaldehyde was added to the mass, followed by stirring for 60 hours at room temperature. 1.6g of white crystals precipitated upon cooling to a lower temperature than 5°C were filtered and collected. The filtrate was twice subjected to extraction with 100 ml of chloroform each time. The mass of two chloroform extracts was washed first with 10 ml of a saturated aqueous solution of sodium bicarbonate and then twice with 10 ml of water, followed by drying with anhydrous sodium sulfate. The chloroform was distilled out under vacuum, obtaining 2.7g of white crystals. The former lot of white crystals weighing 1.6g and the latter lot of white crystals weighing 2.7g were put together. These lots of white crystals were recrystallized from water, providing 3.9g of white needle-like crystals of the desired 2-hydroxy-3-methyl-2-cyclopenten-1-one in 70% yield based on the raw 2-methyl-5-carbomethoxycyclopentanone. The white needle-like crystals displayed the same physicochemical properties as in Example 1.

EXAMPLE 27

A solution prepared by dissolving 2.2g of sodium hydroxide in 40 ml of water was dripped at a lower temperature than 20°C into 7.8g of 2-methyl-5-carbomethoxycyclopentanone. A solution prepared by dissolving 3.45g of sodium nitrite in 10 ml of water was further added to the mixture. The whole mass was stirred 6 hours at room temperature, followed by cooling to a lower temperature than 5°C. After addition of 15 ml of concentrated hydrochloric acid, stirring was continued one more hour at the same temperature. 5.8g of n-butylaldehyde was added, followed by stirring of 60 hours at room temperature. The reaction liquid was twice subjected to extraction with 100 ml of chloroform each time. The mass of two chloroform extracts was washed first with 10 ml of a saturated aqueous solution of sodium bicarbonate and then twice with 10 ml of water, followed by drying with anhydrous sodium sulfate. The chloroform was distilled out, obtaining 5.4g of residual oil. The residual oil was distilled under vacuum to provide 4.3g of substantially colorless distillate. This distillate was immediately solidified. The solidified distillate was recrystallized from water, providing 4.1g of white crystals of the desired 2-hydroxy-3-methyl-2-cyclopenten-1-one in 73% yield based on the raw 2-methyl-5-carbomethoxycyclopentanone. The boiling point of the product was 120° to 122°C/33 mm Hg. The other physicochemical properties of the product were the same as in Example 1.

EXAMPLE 28

A solution prepared by dissolving 0.2g of sodium hydroxide in 40 ml of water was dripped at a lower temperature than 20°C into 8.9g of sodium salt of 2-methyl-5-carbomethoxycyclopentanone obtained in the same manner as in Example 10. A solution prepared by dissolving 3.45g of sodium nitrite in 10 ml of water was further added to the mixture. The whole mass was stirred 6 hours at room temperature, followed by cooling to a lower temperature than 5°C. After addition of 15 ml of concentrated hydrochloric acid, stirring was continued 1 more hour. 24 ml of formalin was added to the mass, followed by stirring of 17 hours at room temperature. 2.7g of white crystals precipitated upon cooling to a lower temperature than 5°C were filtered and collected. The filtrate was twice subjected to extraction with 100 ml of chloroform each time. The mass of two chloroform extracts was washed first with 10 ml of a saturated aqueous solution of sodium bicarbonate and then twice with 10 ml of water, followed by drying with anhydrous sodium sulfate. The chloroform was distilled out under vacuum, providing 2.0g of white crystals. The former lot of white crystals weighing 2.7g and the latter lot of white crystals weighing 2.0g were put together. These lots of white crystals were recrystallized from water, obtaining 4.4g of white crystals of the desired 2-hydroxy-3-methyl-2-cyclopenten-1-one in 79% yield based on the raw sodium salt of 2-methyl-5-carbomethoxycyclopentanone. The white crystals indicated the same physicochemical properties as in Example 1.

What we claim is:

1. A method of preparing 2-hydroxy-3-alkyl-2-cyclopenten-1-one whose chemical structure may be expressed by the general formula

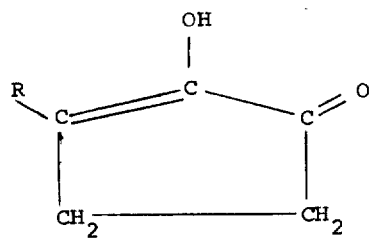

which comprises: reacting (a) 2-alkyl-5-carboalkoxycyclopentanone having a structure represented by the general formula:

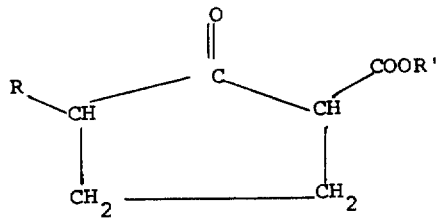

R and R' in the foregoing formulae representing lower alkyl radicals selected from the group consisting of methyl, ethyl, n-propyl and butyl, with (b) a nitrite selected from the group consisting of potassium nitrite and sodium nitrite at a temperature between about 0° to 60°C for a period ranging between about 1 to 60 hours, the mol ratio of nitrite to reactant (a) being between 1:1 and 3:1, in the presence of (c) water in an amount of 200 to 2000 ml per mol of reactant (a) and (d) alkali selected from the group consisting of sodium hydroxide, potassium hydroxide, sodium carbonate and potassium carbonate, the mol ratio of alkali to reactant (a) being between about 1:1 and 3:1, rendering the reaction system acidic at a temperature level lower than room temperature by adding an acid selected from the group consisting of hydrochloric acid and sulfuric acid to the reaction system in an amount of 2.3 to 11 equivalents per mol of reactant (a), and thermally treating the reaction system for hydrolysis at a temperature between about 40° and 100°C.

2. A method according to claim 1, wherein the reaction system rendered acidic is mixed with an aliphatic lower carbonyl compound as an acceptor to carry out oxime exchange reaction, instead of thermally treating said reaction system rendered acidic.

3. A method according to claim 1 wherein 2-alkyl-5-oximinocyclopentanone produced in the reaction system when said system is rendered acidic is separated from said system, and the 2-alkyl-5-oximinocyclopentanone thus separated is thermally hydrolyzed in an acid aqueous solution.

4. A method according to claim 3, wherein the 2-alkyl-5-oximinocyclopentanone is subjected to oxime exchange reaction in the presence of an aliphatic lower carbonyl compound used as an acceptor in an acid aqueous solution in place of being thermally hydrolyzed in said solution.

5. A method according to claim 1, wherein alkali metal salt of the 2-alkyl-5-carboalkoxycyclopentanone is suspended in water and said water suspension is mixed with nitrite for reaction, instead of reacting said 2-alkyl-5-carboalkoxycyclopentanone with nitrite in the presence of water and alkali.

6. A method according to claim 2, wherein alkali metal salt of the 2-alkyl-5-carboalkoxycyclopentanone is suspended in water and said water suspension is mixed with nitrite for reaction, instead of reacting said 2-alkyl-5-carboalkoxycyclopentanone with nitrite in the presence of water and alkali.

7. The method of claim 2 wherein said carbonyl compound is formaldehyde, acetaldehyde, propionaldehyde, butyl aldehyde, acetone or methylethyl ketone.

8. A method according to claim 3 wherein the acid used to render the reaction system acidic is added in an amount of 2 to 6 equivalents per mol of reactant (a).

9. A method according to claim 3 wherein said acid aqueous solution contains 0.3 to 5.0 equivalents of acid per mol of 2-alkyl-5-oximino-cyclopentanone.

10. A method according to claim 3 wherein said acid aqueous solution contains 80 to 3000 ml of water per mol of 2-alkyl-5-oximine-cyclopentanone.

11. A method according to claim 2 wherein the carbonyl compound is added in an amount of at least 1 mol per mol of reactant (a).

12. A method according to claim 2 wherein said oxime exchange reaction is carried out at a temperature between about 0° and 50°C.

13. A method according to claim 12 wherein said oxime exchange reaction is carried out for a period of about 2 hours to three days.

* * * * *